(12) United States Patent
Jackson et al.

(10) Patent No.: US 7,731,738 B2
(45) Date of Patent: Jun. 8, 2010

(54) CANNULATED SCREW

(75) Inventors: Jesse Jackson, Hollaberg, UT (US); Craig Schelling, Liberty, UT (US)

(73) Assignee: Orthopro, LLC, Salt Lake City, UT (US)

( * ) Notice: Subject to any disclaimer, the term of this patent is extended or adjusted under 35 U.S.C. 154(b) by 631 days.

(21) Appl. No.: 11/298,065

(22) Filed: Dec. 9, 2005

(65) Prior Publication Data

US 2007/0162028 A1     Jul. 12, 2007

(51) Int. Cl.
*A61B 17/58*     (2006.01)

(52) U.S. Cl. .................. 606/304; 606/300; 606/311; 606/305; 606/308; 606/318

(58) Field of Classification Search .............. 606/74, 606/75, 311, 312, 318, 300, 301, 302, 303, 606/304, 305, 306, 307, 308, 309, 310, 314, 606/315, 316, 317, 319, 320, 321, 322, 323, 606/324, 325, 326, 327, 328, 329, 330, 331, 606/250–278; 408/204, 227; 411/386, 387.1, 411/387.2, 387.3, 387.4, 387.5, 387.6, 387.7, 411/387.8

See application file for complete search history.

(56) References Cited

U.S. PATENT DOCUMENTS

| | | | |
|---|---|---|---|
| 1,201,864 A | 10/1916 | OverMeyer | |
| 1,330,792 A * | 2/1920 | Frick | 411/387.5 |
| 1,789,060 A | 1/1931 | Weisenbach | |
| 1,869,726 A | 8/1932 | Youngren | |
| 1,997,466 A | 4/1935 | Longfellow | 128/92 |
| 2,020,262 A | 11/1935 | Longfellow | 128/84 |
| 2,024,325 A | 12/1935 | Allen | 128/85 |
| 2,238,870 A | 4/1941 | Haynes | 128/92 |
| 2,250,417 A | 7/1941 | Ettinger | 128/92 |
| 2,251,209 A | 7/1941 | Stader | 128/92 |
| 2,371,519 A | 3/1945 | Haynes | 128/84 |
| 2,388,482 A | 11/1945 | Haynes | 10/140 |

(Continued)

FOREIGN PATENT DOCUMENTS

DE     3722595     1/1989

(Continued)

OTHER PUBLICATIONS

ORTHOFIX Modulsystem—General Application Instructions. Jan. 1996, 28 pages.

(Continued)

*Primary Examiner*—Eduardo C Robert
*Assistant Examiner*—Jan Christopher Merene
(74) *Attorney, Agent, or Firm*—Workman Nydegger (57) ABSTRACT

A cannulated screw which maintains compression at the interface between two or more materials in a medical or other setting to effectively secure bone to bone while minimizing separation between the bones and the securement interface. The cannulated screw has a flattened tip, which enables the cannulated screw to more readily bore or self-tap into bone or other material. The flattened tip of the cannulated screw comprises a plurality of cutting teeth which facilitate boring of the flattened tip of the cannulated screw into the material into which the screw is being inserted. In one embodiment, three progressive cutting teeth are provided on the flattened tip of the cannulated screw.

18 Claims, 7 Drawing Sheets

U.S. PATENT DOCUMENTS

| | | | | |
|---|---|---|---|---|
| 2,391,537 | A | 12/1945 | Anderson | 128/84 |
| 2,393,694 | A | 1/1946 | Kirschner | 128/84 |
| 2,406,987 | A | 9/1946 | Anderson | 128/85 |
| 2,435,850 | A | 2/1948 | Siebrandt | 128/92 |
| 2,439,995 | A | 4/1948 | Thrailkill | 128/84 |
| 2,847,885 | A * | 8/1958 | Wagner | 408/59 |
| 3,130,763 | A * | 4/1964 | Schlosser et al. | 408/205 |
| 3,395,603 | A * | 8/1968 | Skierski | 411/387.8 |
| 3,572,183 | A * | 3/1971 | Mellone | 408/227 |
| 3,877,424 | A | 4/1975 | Murray | 128/92 A |
| 4,023,448 | A * | 5/1977 | Bertini | 76/112 |
| 4,160,397 | A * | 7/1979 | Bertini | 83/661 |
| 4,212,568 | A * | 7/1980 | Minicozzi | 407/12 |
| 4,273,116 | A | 6/1981 | Chiquet | 128/92 A |
| 4,312,336 | A | 1/1982 | Danieletto et al. | 128/92 A |
| RE31,809 | E | 1/1985 | Danieletto et al. | 128/92 |
| 4,502,473 | A | 3/1985 | Harris et al. | 128/92 A |
| 4,537,185 | A * | 8/1985 | Stednitz | 606/304 |
| 4,554,915 | A | 11/1985 | Brumfield | 128/92 A |
| 4,570,625 | A | 2/1986 | Harris et al. | 128/92 G |
| 4,604,997 | A | 8/1986 | De Bastiani et al. | 128/92 A |
| 4,611,586 | A | 9/1986 | Agee et al. | 128/92 |
| 4,621,627 | A | 11/1986 | DeBastiani et al. | 128/92 ZZ |
| 4,628,919 | A | 12/1986 | Clyburn | 128/92 |
| 4,628,921 | A | 12/1986 | Rousso | 128/92 |
| 4,643,177 | A | 2/1987 | Sheppard et al. | 128/84 C |
| 4,782,842 | A | 11/1988 | Fietti, Jr. | 128/92 |
| 4,828,277 | A | 5/1989 | De Bastiani et al. | 279/1 SG |
| 4,848,368 | A | 7/1989 | Kronner | 128/92 |
| 4,919,119 | A | 4/1990 | Jonsson et al. | 606/54 |
| 4,920,959 | A | 5/1990 | Witzel et al. | 606/53 |
| 4,922,896 | A | 5/1990 | Agee et al. | 606/55 |
| 4,946,179 | A | 8/1990 | De Bastiani et al. | 279/1 SG |
| 4,988,349 | A | 1/1991 | Pennig | 606/58 |
| 5,019,077 | A | 5/1991 | De Bastiani et al. | 606/54 |
| 5,026,374 | A | 6/1991 | Dezza et al. | 606/72 |
| 5,047,030 | A * | 9/1991 | Draenert | 606/65 |
| 5,074,865 | A | 12/1991 | Fahmy | 606/54 |
| 5,098,432 | A | 3/1992 | Wagenknecht | 606/54 |
| 5,108,394 | A | 4/1992 | Kurokawa | 606/59 |
| 5,122,140 | A | 6/1992 | Asche et al. | 606/55 |
| 5,122,145 | A | 6/1992 | Fishbane | 606/102 |
| 5,152,280 | A | 10/1992 | Danieli | 128/54 |
| 5,160,335 | A | 11/1992 | Wagenknecht | 606/59 |
| 5,167,661 | A | 12/1992 | Wagenknecht | 606/54 |
| 5,196,014 | A | 3/1993 | Lin | 606/61 |
| 5,207,676 | A | 5/1993 | Canadell et al. | 606/54 |
| 5,213,452 | A * | 5/1993 | Kirby | 407/42 |
| 5,281,224 | A | 1/1994 | Faccioli et al. | 606/62 |
| 5,292,322 | A | 3/1994 | Faccioli et al. | 606/59 |
| 5,301,177 | A | 4/1994 | Kumakura | 369/75.2 |
| 5,304,177 | A | 4/1994 | Pennig | 606/58 |
| 5,318,571 | A | 6/1994 | Benson | 606/102 |
| 5,320,622 | A | 6/1994 | Faccioli et al. | 606/58 |
| 5,320,623 | A | 6/1994 | Pennig | 606/59 |
| 5,330,474 | A | 7/1994 | Lin | 606/61 |
| 5,334,202 | A | 8/1994 | Carter | 606/58 |
| 5,342,360 | A | 8/1994 | Faccioli et al. | 606/59 |
| 5,376,090 | A | 12/1994 | Pennig | 606/54 |
| 5,382,248 | A | 1/1995 | Jacobson et al. | 606/60 |
| 5,397,322 | A | 3/1995 | Campopiano | 606/57 |
| 5,405,347 | A | 4/1995 | Lee et al. | 606/54 |
| RE34,985 | E | 6/1995 | Pennig | 606/58 |
| 5,429,637 | A | 7/1995 | Hardy | 606/54 |
| 5,433,720 | A | 7/1995 | Faccioli et al. | 606/87 |
| 5,437,667 | A | 8/1995 | Papierski et al. | 606/55 |
| 5,451,225 | A | 9/1995 | Ross, Jr. et al. | 606/59 |
| 5,454,810 | A | 10/1995 | Pohl et al. | 606/59 |
| 5,536,121 | A * | 7/1996 | McSherry | 411/31 |
| 5,540,688 | A | 7/1996 | Navas | 606/61 |
| 5,545,162 | A | 8/1996 | Huebner | 606/57 |
| 5,591,164 | A | 1/1997 | Nazre et al. | 606/59 |
| 5,601,551 | A | 2/1997 | Taylor et al. | 606/54 |
| 5,603,717 | A | 2/1997 | Benson | 606/102 |
| 5,620,442 | A | 4/1997 | Bailey et al. | 606/54 |
| 5,620,449 | A | 4/1997 | Faccioli et al. | 606/98 |
| 5,624,440 | A | 4/1997 | Huebner | 606/59 |
| 5,630,814 | A | 5/1997 | Ross, Jr. et al. | 606/59 |
| 5,658,283 | A | 8/1997 | Huebner | 606/57 |
| 5,662,648 | A | 9/1997 | Faccioli et al. | 606/54 |
| 5,662,649 | A | 9/1997 | Huebner | 606/57 |
| 5,662,650 | A | 9/1997 | Bailey et al. | 606/59 |
| 5,681,318 | A | 10/1997 | Pennig et al. | 606/98 |
| 5,688,271 | A | 11/1997 | Faccioli et al. | 606/54 |
| 5,690,633 | A | 11/1997 | Taylor et al. | 606/73 |
| 5,707,370 | A | 1/1998 | Berki et al. | 606/59 |
| 5,709,681 | A | 1/1998 | Pennig | 606/54 |
| 5,728,096 | A | 3/1998 | Faccioli et al. | 606/54 |
| 5,743,898 | A | 4/1998 | Bailey et al. | 606/54 |
| 5,755,794 | A | 5/1998 | Benson | 623/16 |
| 5,766,179 | A | 6/1998 | Faccioli et al. | 606/98 |
| 5,769,851 | A | 6/1998 | Veith | 606/57 |
| 5,788,695 | A | 8/1998 | Richardson | 606/57 |
| 5,792,076 | A | 8/1998 | Orsak et al. | 606/587 |
| 5,803,924 | A | 9/1998 | Oni et al. | 606/54 |
| 5,814,050 | A | 9/1998 | Benson | 606/102 |
| 5,827,282 | A | 10/1998 | Pennig | 606/54 |
| 5,881,878 | A | 3/1999 | Faccioli et al. | 206/438 |
| 5,885,289 | A | 3/1999 | Muller | 606/71 |
| 5,902,302 | A | 5/1999 | Berki et al. | 606/59 |
| 5,921,985 | A | 7/1999 | Ross, Jr. et al. | 606/59 |
| 5,941,877 | A | 8/1999 | Viegas et al. | 606/55 |
| 5,951,556 | A | 9/1999 | Faccioli et al. | 606/65 |
| 5,968,043 | A | 10/1999 | Ross, Jr. et al. | 606/56 |
| 5,976,125 | A | 11/1999 | Graham | 606/32 |
| 5,976,134 | A | 11/1999 | Huebner | 606/59 |
| 5,976,136 | A | 11/1999 | Bailey et al. | 606/61 |
| 6,010,501 | A | 1/2000 | Raskin et al. | 606/54 |
| 6,015,413 | A | 1/2000 | Faccioli et al. | 606/104 |
| 6,024,745 | A | 2/2000 | Faccioli et al. | 606/54 |
| 6,027,506 | A | 2/2000 | Faccioli et al. | 606/98 |
| 6,030,162 | A * | 2/2000 | Huebner | 411/413 |
| 6,036,691 | A | 3/2000 | Richardson | 606/57 |
| 6,102,911 | A | 8/2000 | Faccioli et al. | 606/54 |
| 6,126,661 | A | 10/2000 | Faccioli et al. | 606/64 |
| 6,143,012 | A | 11/2000 | Gausepohl | 606/185 |
| 6,162,223 | A | 12/2000 | Orsak et al. | 606/59 |
| 6,162,224 | A | 12/2000 | Huebner | 606/59 |
| 6,171,307 | B1 | 1/2001 | Orlich | 606/53 |
| 6,171,308 | B1 | 1/2001 | Bailey et al. | 606/54 |
| 6,171,309 | B1 | 1/2001 | Huebner | 606/57 |
| 6,217,577 | B1 | 4/2001 | Hofmann | 606/57 |
| 6,235,029 | B1 | 5/2001 | Faccioli et al. | 606/54 |
| 6,245,071 | B1 | 6/2001 | Pierson | 606/58 |
| 6,258,092 | B1 * | 7/2001 | Dall | 606/292 |
| 6,277,118 | B1 | 8/2001 | Grant et al. | 606/54 |
| 6,306,140 | B1 * | 10/2001 | Siddiqui | 606/315 |
| 6,328,737 | B1 | 12/2001 | Moorcroft et al. | 606/57 |
| 6,340,361 | B1 | 1/2002 | Kraus et al. | 606/59 |
| 6,364,824 | B1 | 4/2002 | Fitzsimmons | 600/13 |
| 6,409,729 | B1 | 6/2002 | Martinelli et al. | 606/59 |
| 6,413,258 | B1 | 7/2002 | Bernhardt, Jr. | 606/61 |
| 6,423,061 | B1 | 7/2002 | Bryant | 606/57 |
| 6,428,540 | B1 | 8/2002 | Claes et al. | 606/53 |
| 6,435,780 | B1 * | 8/2002 | Flynn | 407/53 |
| 6,461,358 | B1 | 10/2002 | Faccioli et al. | 606/57 |
| 6,482,206 | B2 | 11/2002 | Schoenefeld | 606/59 |
| 6,491,694 | B1 | 12/2002 | Orsak | 606/57 |
| 6,500,177 | B1 | 12/2002 | Martinelli et al. | 606/57 |
| 6,565,564 | B2 | 5/2003 | Hoffman et al. | 606/59 |
| 6,565,568 | B1 | 5/2003 | Rogozinski | 606/61 |
| 6,605,088 | B1 | 8/2003 | St. Onge et al. | 606/54 |
| 6,613,049 | B2 | 9/2003 | Winquist et al. | 606/59 |
| 6,635,059 | B2 * | 10/2003 | Randall et al. | 606/916 |

| | | | |
|---|---|---|---|
| 6,678,562 B1 | 1/2004 | Tepper et al. ............... 607/51 |
| 6,699,251 B1 | 3/2004 | Venturini .................... 606/73 |
| 6,709,433 B1 | 3/2004 | Schoenefeld ................ 606/57 |
| 6,722,368 B1 | 4/2004 | Shaikh ................ 128/207.15 |
| 6,749,611 B2 | 6/2004 | Venturini et al. ............. 606/54 |
| 6,770,075 B2 | 8/2004 | Howland ..................... 606/61 |
| 6,786,903 B2* | 9/2004 | Lin ............................. 606/23 |
| 7,037,309 B2* | 5/2006 | Weil et al. .................... 606/304 |
| 7,074,222 B2* | 7/2006 | Westerkull .................. 606/312 |
| 2001/0034520 A1 | 10/2001 | Enayati ....................... 606/59 |
| 2002/0004659 A1 | 1/2002 | Boudard et al. .............. 606/54 |
| 2002/0115998 A1 | 8/2002 | Schoenefeld ................ 606/59 |
| 2002/0151892 A1 | 10/2002 | Walulik et al. ............... 606/57 |
| 2003/0028193 A1* | 2/2003 | Weil et al. ..................... 606/73 |
| 2003/0109879 A1 | 6/2003 | Orsak .......................... 606/57 |
| 2003/0139744 A1 | 7/2003 | Berki et al. .................. 606/57 |
| 2004/0106925 A1* | 6/2004 | Culbert ........................ 606/73 |
| 2004/0230195 A1* | 11/2004 | Kaikkonen et al. ............ 606/72 |
| 2005/0149031 A1* | 7/2005 | Ciccone et al. .............. 606/73 |
| 2006/0217727 A1* | 9/2006 | Munro et al. ................. 606/73 |
| 2007/0208344 A1* | 9/2007 | Young .......................... 606/61 |

FOREIGN PATENT DOCUMENTS

| | | |
|---|---|---|
| EP | 0011258 | 5/1980 |
| EP | 0 240 034 B1 | 10/1987 |
| EP | 0 261 252 | 3/1988 |
| EP | 0 314 021 A2 | 5/1989 |
| EP | 0 424 292 B1 | 4/1991 |
| EP | 0 216 563 B1 | 6/1991 |
| EP | 0 604 697 A1 | 7/1994 |
| EP | 0 685 206 A1 | 12/1995 |
| EP | 0 734 232 B1 | 2/1996 |
| EP | 0 717 968 A2 | 6/1996 |
| EP | 0 779 795 B1 | 6/1997 |
| EP | 0 609 409 B1 | 9/1998 |
| EP | 0 858 781 A3 | 5/1999 |
| FR | 2557933 | 7/1985 |
| NL | 8802463 | 5/1990 |
| WO | WO 89/09031 | 10/1989 |
| WO | WO 90/07305 | 7/1990 |
| WO | WO 90/11727 | 10/1990 |
| WO | WO 91/00111 | 8/1991 |
| WO | WO 94/02078 | 2/1994 |
| WO | WO 94/23662 | 10/1994 |
| WO | WO 95/04504 | 2/1995 |
| WO | WO 95/10240 | 4/1995 |
| WO | WO 95/16401 | 6/1995 |
| WO | WO 96/17557 | 6/1996 |
| WO | WO 96/35385 | 11/1996 |
| WO | WO 98/46156 | 10/1998 |
| WO | WO 98/51227 | 11/1998 |
| WO | WO 99/02097 | 1/1999 |
| WO | WO 99/04714 | 2/1999 |
| WO | WO 99/22661 | 5/1999 |
| WO | WO 99/30626 | 6/1999 |
| WO | WO 00/40163 | 7/2000 |

OTHER PUBLICATIONS

Dr. Joachim Pfeil, *Unilateral Fixation Techniques in Limb Deformity Corrections*, 1994. 48 pages.

Dr. Dietmar Pennig, *The Pennig Dynamic Wrist Fixator—Orthofix*. Mar. 25, 1992, 47 pages.

Orthofix Modulsystem, *These could drive you to distraction . . . callus distraction with the Limb Reconstruction System*, Jul. 1997, prior edition before May 21, 1997, 16 pages.

Professor M. Saleh, *Operative Technique*, Limb Reconstruction System, Orthofix Modulsystem, Mar. 1998, prior edition before May 21, 1997, 67 pages.

US 6,030,385, 02/2000, Faccioli et al. (withdrawn)

* cited by examiner

CANNULATED SCREW

BACKGROUND OF THE INVENTION

1. The Field of the Invention

The present invention relates to a threaded fastener, such as a screw. More particularly, the present invention relates to a cannulated screw having a flattened tip to facilitate securement of bone, tissue, or other materials in a medical, industrial, or similar setting.

2. The Relevant Technology

Mechanical fasteners, such as screws, bolts, nails, and the like, have long been utilized in industrial, construction, medical, and other settings to facilitate the securement of one or more members in a desired placement or configuration. For example, screws can be utilized to secure lumber, metal braces, and other materials in a particular setting. Screws typically comprise a head, a threaded portion, and a tip. The head is typically configured to accommodate a rotational tool which provides the torque necessary to drive the screw into the material into which the screw is desired to be inserted. The tip and threads of the screw are designed to allow for self boring of the screw into the material into which it is to be inserted. The tip of the screw is configured to bore into the material in a manner that allows engagement of the threads within the material. The threads, once engaged by the material, provide a forward force to facilitate additional forward movement of the screw in a perpendicular vector relative to the front plane of the material.

One difficulty that is associated with existing screws, is that the tip of such screws typically have a fairly sharp point to allow for self tapping of the screw into the material. The pointed tip of the screw can have a variety of lengths and configurations based on the implementation for which the screw is designed. In many implementations, the length of such tips can be fairly long. For example, in some designs the length of the tip is approximately the equivalent of the distance between three threads along the shaft of the screw. The tip of the screw is typically sharpened such that as the user provides sufficient normal force, the sharpened tip will puncture sufficiently into the material to allow for the engagement of the threads in the material.

When a user is utilizing the screw to affix a member, board, or other material to a secondary member, once the screw has fully penetrated the material or member, the tip of the screw will then begin to enter the secondary member to which the primary member is being secured. As a result, the amount of normal force that is needed to begin self tapping of the tip of the screw into the secondary member will typically force the secondary member a certain amount of displacement away from the primary member resulting in a gap at the interface of the two members. Such gaps can be undesirable as the gaps can limit the strength and aesthetics of the bond between the two members. The gap resulting from the configuration and use of such screws can be problematic and frustrating to a user who is attempting to provide effective and close contact between the two members.

The configuration of the tip of such screws and the resulting gaps can be particularly problematic in a medical setting. One reason that such gaps can be undesirable is that, in a medical setting, screws are typically utilized to secure bone to bone or tissue or another material to bone. As a result, spacing or gaps between the bone securement interface can prevent secure bonding between the two pieces of bone. This can be particularly problematic where the two pieces of bone comprise fragments of a broken bone. Any space between the two bones can result in prolonged healing and complete ossification of the space between the bones which can result in changes to the shape of the bone. Such changes to the shape of the bone can alter the mechanics of the bone in a manner that could weaken or result in changes to the biomechanics of the user's body. Additionally, such spacing can result in abnormal growth in the bone that can create additional complications.

An additional complication that is created in the use of such screws in securing bone segments to one another relates to the nature of bones. Bone typically comprises an outer cortical portion and an inner cancellous bone layer. The cortical bone layer is substantially harder and stronger than the typically softer and more porous cancellous portion. As a result, the cortical bone provides the desired anchoring characteristics for embedding screws and other medical fasteners. While the cortical bone layer is stronger than the cancellous portion, the cortical portion is typically quite thin compared to the cancellous portion.

The cortical bone layer typically lies on the outer boundary of the bone. As a result, where a screw has been threaded through two different segments of bone, the tip of the screw will begin to exit from the outward cortical portion of the bone opposite the bone/bone interface before the threads of the screw have engaged the cortical layer. In other words, the threaded portion of the screw may not have entered the rearward cortical bone layer before advancement of the screw must be stopped. Protrusion of the tip of the screw past the outer boundary of the cortical bone layer can be quite problematic. For example, protrusion of the tip of the screw from the cortical bone layer may result in contact of the tip of the screw with connective tissue, muscle tissue, or other tissue adjacent the bone that may result in severe pain and/or complications in the patient as a result of placement of the screw. In other words, the configuration of many existing medical screw-type fasteners is ill-suited for the securement of bone to bone or other materials to bone within the body. Many industrial and construction type screw-type fasteners suffer from the same type of deficiencies in their desired use setting as that described with relation to screws utilized in medical settings.

BRIEF SUMMARY OF THE INVENTION

The present invention relates to a cannulated screw which maintains compression at the interface between two or more materials in a medical or other setting. For example, the cannulated screw can be utilized to effectively secure bone to bone while minimizing separation between the bones at the securement interface. The present invention also relates to a cannulated screw having a flattened tip, which enables the cannulated screw to more readily bore or self-tap into bone or other material.

According to one embodiment of the present invention, the flattened tip of the cannulated screw comprises a plurality of cutting teeth which facilitate boring of the flattened tip of the cannulated screw into the material into which the screw is being inserted. In one embodiment, three cutting teeth are provided on the flattened tip of the cannulated screw. The cutting teeth provide progressive cutting surfaces. In one embodiment, a first cutting tooth has the lowest height and the smallest cutting diameter. When the first cutting tooth contacts a bone or other material a relatively small amount of material is removed and a primary amount of self-tapping is instigated.

A second tooth is provided to follow the first tooth. The second tooth has an intermediate height and an intermediate cutting diameter, such that the second tooth removes an amount of material in addition to the amount of material removed by the first tooth. A third tooth has the greatest cutting height and the largest cutting diameter. The third tooth removes yet an additional amount of material above and beyond that which was removed by the second tooth. The third tooth facilitates threading of the threads of the screw into the material to facilitate additional self-tapping and forward advancement of the screw into the material.

In one embodiment, the tip of the screw has a flattened configuration to reduce the distance between the uppermost surface of the tip and the average plane of the first thread of the shaft such that additional threads can engage a cortical layer of a bone before the self-boring tip exits the outward surface of the cortical layer. In one embodiment, the distance between the uppermost surface of the tip and the uppermost surface of the threads of the shaft is less than the one and half times the distance between adjacent threads on the shaft.

In one embodiment, a plurality of teeth are provided and a single thread extends along a portion, or all of the length, of the cannulated screw. In another embodiment, more than one thread is utilized with the plurality of teeth to facilitate self-tapping of the screw into the material into which it is to be inserted. In another embodiment, the cannulated screw includes a tip which is configured to cut on contact with the material to minimize and/or prevent separation of materials at a bone securement interface. For example, in a bone/bone implementation, the flattened configuration of the tip of the screw allows the threads of the screw to penetrate into the cortical layer before the tip of the screw exits the rear portion of the cortical bone. In yet another embodiment, the cannulated screw includes a cannula which facilitates placement of the cannulated screw at a desired position within a patient in connection with a guidewire, suture, or similar mechanism.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to a cannulated screw which maintains compression at the interface between two or more materials in a medical or other setting. For example, the cannulated screw can be utilized to effectively secure bone to bone while minimizing separation between the bones at the securement interface. The present invention also relates to a cannulated screw having a flattened tip, which enables the cannulated screw to more readily bore or self-tap into bone or other material.

According to one embodiment of the present invention, the flattened tip of the cannulated screw comprises a plurality of cutting teeth which facilitate boring of the flattened tip of the cannulated screw into the material into which the screw is being inserted. In one embodiment, three cutting teeth are provided on the flattened tip of the cannulated screw. The cutting teeth provide progressive cutting surfaces. In one embodiment, a first cutting tooth has the lowest height and the smallest cutting diameter. When the first cutting tooth contacts a bone or other material a relatively small amount of material is removed and a primary amount of self-tapping is instigated.

A second tooth is provided to follow the first tooth. The second tooth has an intermediate height and an intermediate cutting diameter, such that the second tooth removes an amount of material in addition to the amount of material removed by the first tooth. A third tooth has the greatest cutting height and the largest cutting diameter. The third tooth removes yet an additional amount of material above and beyond that which was removed by the second tooth. The third tooth facilitates threading of the threads of the screw into the material to facilitate additional self-tapping and forward advancement of the screw into the material.

In one embodiment, the tip of the screw has a flattened configuration to reduce the distance between the uppermost surface of the tip and the average plane of the first thread of the shaft such that additional threads can engage a cortical layer of a bone before the self-boring tip exits the outward surface of the cortical layer. In one embodiment, the distance between the uppermost surface of the tip and the uppermost surface of the threads (distance $d^1$) of the shaft is less than the one and half times the distance between adjacent threads on the shaft (distance $d^2$).

In one embodiment, a plurality of teeth are provided and a single thread extends along a portion, or all of the length, of the cannulated screw. In another embodiment, more than one thread is utilized with the plurality of teeth to facilitate self-tapping of the screw into the material into which it is to be inserted. In another embodiment, the cannulated screw includes a tip which is configured to cut on contact to minimize and/or prevent separation of materials at a material/material interface. For example, in a bone/bone implementation, the flattened configuration of the tip of the screw allows the threads of the screw to penetrate into the cortical layer before the tip of the screw exits the rear portion of the cortical bone. In yet another embodiment, the cannulated screw includes a cannula which facilitates placement of the cannulated screw at a desired position within a patient in connection with a guidewire, suture, or similar mechanism.

Figure 1:
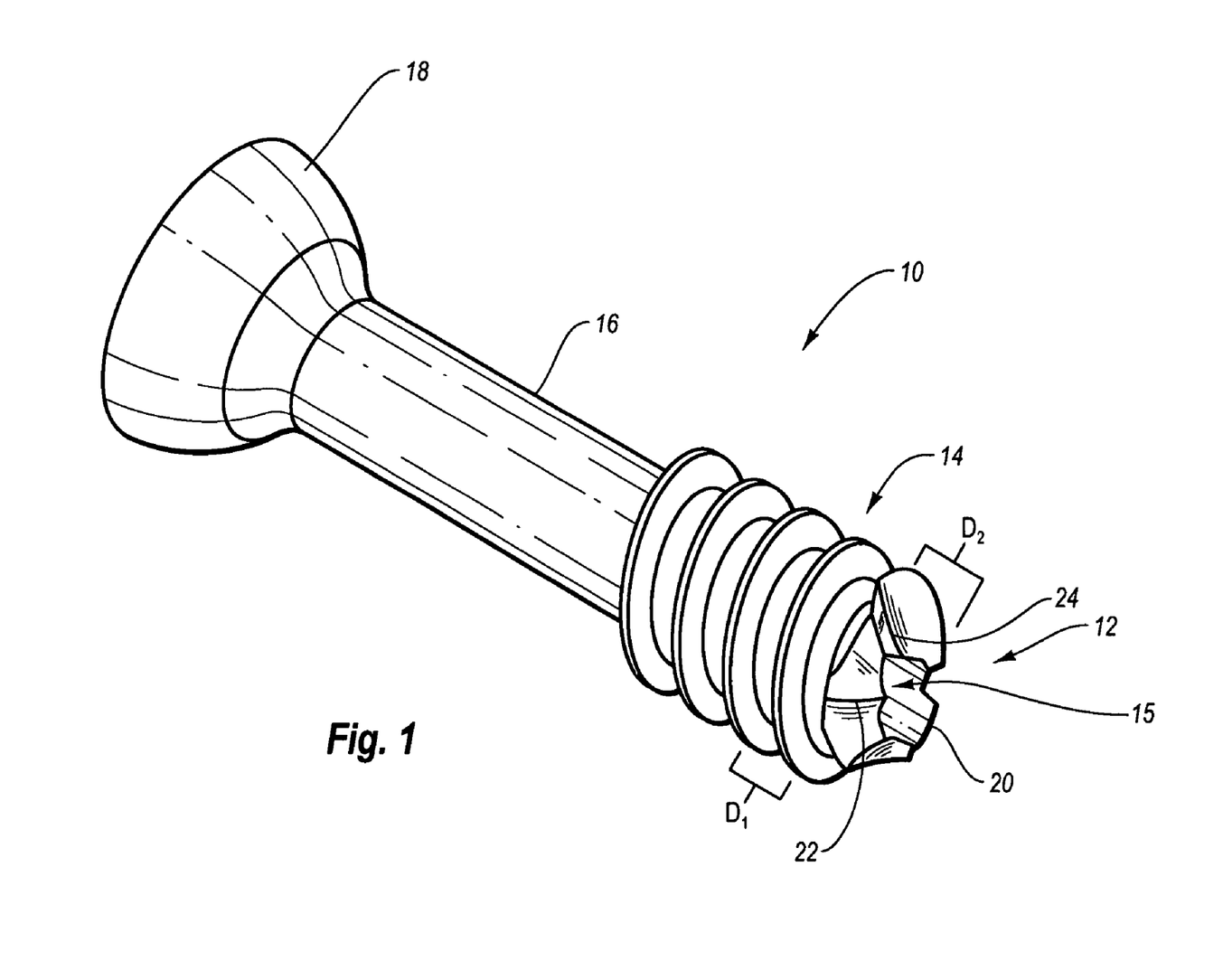
FIG. 1 is a perspective view of a cannulated screw, according to one embodiment of the present invention.

FIG. 1 is a perspective view of a cannulated screw 10, according to one embodiment of the present invention. Cannulated screw 10 is utilized to secure materials to bone, or two bone segments to one another in a medical setting. In the illustrated embodiment, cannulated screw 10 comprises a flattened tip 12, threads 14, cannula 15, a neck 16, and a head 18. Flattened tip 12 is configured such that head 18 is positioned at one end of the cannulated screw 10, flattened tip 12 is positioned at the end of cannulated screw 10 opposite head 18, and threads 14 are positioned adjacent the flattened tip 12. Cannula 15 comprises a channel extending from flattened tip 12 to head 18 along the length of cannulated screw 10. In the illustrated embodiment, the distal most extremity of flattened tip 12 extends only a short distance away from threads 14 to allow for cutting or self-tapping of flattened tip 12 into the material in which cannulated screw 10 is to be inserted. For example, in one embodiment, the distance between the uppermost surface of the tip and the uppermost surface of the threads (distance $d^1$) of the shaft is less than the one and half times the distance between adjacent threads on the shaft (distance $d^2$). In another embodiment, the distance between the uppermost surface of the tip and the uppermost surface of the threads (distance $d^1$) of the shaft is less than the distance between adjacent threads on the shaft (distance $d^2$).

Flattened tip 12 is configured to begin tapping of the cannulated screw 10 into the material in which cannulated screw 10 is being inserted, such that threads 14 can engage the material and continue the progress of cannulated screw 10 into the material. In the illustrated embodiment, threads 14 comprise a single series of threads which are tapped utilizing flattened tip 12. Threads 14 engage the material, such as bone, tissue, or medical hardware, which are to be secured utilizing cannulated screw 10. Threads 14 are provided with a gradation allowing for the effective securement and advancement of cannulated screw 10 once threads 14 have engaged the material into which cannulated screw 10 is being inserted.

Cannula 15 comprises a channel extending from flattened tip 12 to head 18 along the length of cannulated screw 10. Cannula 15 accommodates a thread, suture, guidewire or similar filament or other member permitting a practitioner to insert cannulated screw 10 to a desired position in a patient. The use of cannula 15 allows for the insertion of cannulated screw 10 while requiring minimal cutting or other invasive procedures into the patient. For example, a small incision can be made into the skin of the patient. A guide wire can be inserted into the patient that includes a cutting tip for boring a pilot hole into cartilage, bone or other tissue of the patient. The guidewire can then be threaded along the length of the cannula 15 allowing the cannulated screw 10 to be advanced to the desired position within the patient. The cannulated screw can then be threaded into the bone or other tissue of the patient.

Neck 16 comprises the portion along the shaft of cannulated screw 10 that is devoid of threads 14. Neck 16 typically corresponds with a portion of the cannulated screw that does not necessitate bonding with the material to which cannulated screw 10 is being inserted. For example, threads 14 facilitate advancement of cannulated screw 10 into bone, tissue, or other material. Threads 14 are configured to terminate in a basal material, such as a bone, to which a secondary bone or other material is to be secured. Typically the secondary bone or other material is maintained in contact with the bone or other basal material in which threads 14 of cannulated screw 10 are secured. Head 18 facilitates such contact by providing compression against an outside surface or other contact surface of the bone or other material to maintain its contact with the basal material or bone in which threads 14 are inserted.

In the illustrated embodiment, flattened tip 12 includes a first cutting tooth 20, a second cutting tooth 22, and a third cutting tooth 24. First cutting tooth 20, second cutting tooth 22, and third cutting tooth 24 are examples of a plurality of cutting teeth which are utilized to cut on contact with the material into which cannulated screw 10 is being inserted. In the illustrated embodiment, first cutting tooth 20 provides an initial cut into the material into which cannulated screw 10 is being inserted. Typically, first cutting tooth 20 has the smallest cutting diameter and the lowest overall height, facilitating efficient and complete cutting of the material as desired to begin boring of the cannulated screw 10 into the material.

Typically, the second cutting tooth 22 provides a somewhat larger cutting surface. The second cutting tooth 22 can include an intermediate cutting diameter and an intermediate cutting height, which removes a slightly larger amount of material from that which is removed by the first cutting tooth 20. The third cutting tooth has the greatest overall cutting surface. Third cutting tooth 24 can have the greatest cutting height and largest cutting diameter. This allows third cutting tooth 24 to remove a larger amount of material than that which was removed by the second cutting tooth. In this manner, first cutting tooth 20, second cutting tooth 22, and third cutting tooth 24 provide a progressive material removal system which minimizes chipping or breakage of the material, for example in the case of bone, while providing effective self-tapping of the flattened tip 12 into material in which cannulated screw 10 is being inserted. Additionally, by providing a plurality of progressive cutting teeth, first cutting tooth 20, second cutting tooth 22, and third cutting tooth 24, provide cutting on contact with the material into which cannulated screw 10 is being inserted, effectively minimizing normal forces against the material before boring or self-tapping of the screw is started, which can result in separation or damage to such tissue or material.

As will be appreciated by those skilled in the art, a variety of types and configurations of cannulated screws can be utilized without departing from the scope and spirit of the present invention. For example, in one embodiment the cannulated screw includes a flattened tip having first and second cutting teeth only. In another embodiment, the cannulated screw includes a cutting tip having a single cutting tooth. In another embodiment, the cannulated screw includes a cutting tip having more than three cutting teeth. In another embodiment, the cannulated screw includes threads along the entire shaft of the cannulated screw. In another embodiment, the cannulated screw includes a plurality of threads corresponding with one or more of the plurality of the cutting teeth. In yet another embodiment, a cannulated screw, or flattened tip screw not having a cannula, can be used in a non-medical environment, such as construction, industrial, or other implementations. In another embodiment, a screw having a plurality of cutting teeth is provided that does not include a cannula. In another embodiment, a cannula is provided which can be utilized in combination with a guidewire tool which provides a pilot hole. The pilot hole can correspond with the diameter of the cannula allowing the cutting teeth of the flattened tip to remove an amount of material in addition to that removed by the pilot hole to create a channel for the insertion of the cannulated screw.

Figure 2:
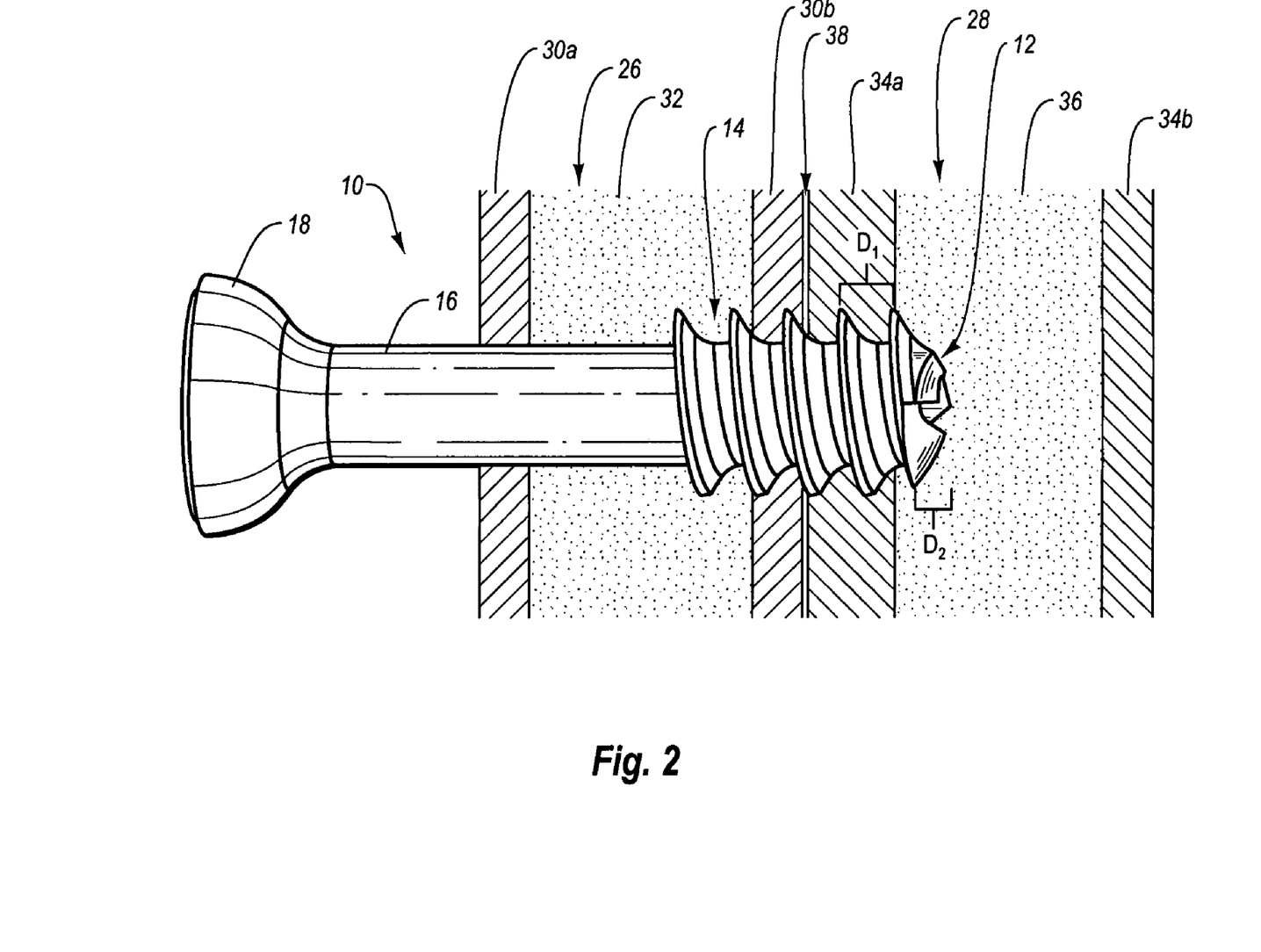
FIG. 2 illustrates a cannulated screw in an exemplary operating environment depicting the cannulated screw securing one bone to a second bone.

FIG. 2 is side view of the cannulated screw 10 being utilized in an illustrative operating environment, according to one embodiment of the present invention. In the illustrated embodiment, cannulated screw 10 is shown being inserted into a first bone segment 26 and a second bone segment 28. In the illustrated embodiment, first bone segment 26 is being secured to second bone segment 28 utilizing cannulated screw 10. First bone segment 26 includes cortical bone layers 30a, b and a cancellous bone layer 32.

Second bone segment 28 includes cortical bone layers 34a, b and a cancellous bone layer 36. Cortical bone layers 30a, b and 34a, b are substantially denser and more rigid than cancellous bone layers 32 and 36. This is largely due to the characteristics of cortical bone, which is much denser and more rigid in configuration than cancellous bone layers, which are typically more porous. The more porous nature of cancellous bone layers renders them less effective as an anchoring substrate for materials, such as a cannulated screw 10. In one illustrative embodiment, the cortical bone layers are approximately two millimeters thick, while the cancellous bone layers are more than twice the thickness of the cortical bone layers.

The configuration of flattened tip 12 allows for effective cutting and penetration of cannulated screw 10 into a cortical bone layer upon contact of flattened tip 12 with the cortical bone layer. Additionally, the configuration of flattened tip 12 allows for anchoring of one or more threads 14 of cannulated screw 10 into the cortical bone layer before the cutting teeth 22 and 24 protrude from the opposite side of the cortical bone layers. This can be helpful with respect to cortical bone layer 34b. Cortical bone layer 34b provides a secondary level of anchoring for the threads of cannulated screw 10 that can facilitate securement of the cannulated screw into the bone. By providing a flattened tip 12, additional turns of the cannulated screw can anchor additional threads 14 into cortical bone layer 34b before flattened tip 12 protrudes from the opposite side of cortical bone layer 34b. This can minimize protruding of the tip of a screw that can result in irritation and/or pain in the tissues positioned adjacent second bone segment 28. In other words, flattened tip 12 allows for more effective securement of cannulated screw 10 into second bone segment 28. Flattened tip 12 allows for such securement by providing for greater engagement of threads 14 into cortical bone layer 34b before the flattened tip 12 of cannulated screw 10 extends outside the outer periphery of second bone segment 28.

As previously discussed, flattened tip 12 and the plurality of cutting teeth 20, 22, 24 (see FIG. 1) of flattened tip 12 begin cutting and penetration of the material into which cannulated screw 10 is being inserted upon contact with the flattened tip 12. This provides for engagement of the cutting teeth and threads of cannulated screw 10 upon contact of flattened tip 12 with the material. By cutting on contact with the material into which cannulated screw 10 is being inserted, separation between materials or members that are being secured to one another utilizing cannulated screw 10 is minimized. For example, in the illustrated embodiment, as flattened tip 12 of cannulated screw 10 protrudes from cortical bone layer 30b it comes in contact with cortical bone layer 34a of second bone segment 28 at the bone securement interface 38.

As flattened tip 12 comes in contact with cortical bone layer 34a, flattened tip 12 begins cutting and boring into cortical bone layer 34a in a manner that maintains compression at the bone securement interface minimizing separation between cortical bone layer 34a and cortical bone layer 34b. This facilitates effective and desired securement of first bone segment 26 to second bone segment 28. By maintaining a minimal displacement between cortical bone layer 30b and cortical bone layer 34a, a stronger and more optimized securement of first bone segment 26 to second bone segment 28 is maintained. This is particularly important where the first bone segment and a second bone segment comprise portions of a broken bone that are being re-secured during an operation to restore the integrity and strength of a bone that has been broken.

As will be appreciated by those skilled in the art, a variety of types and configurations of cannulated screws can be utilized in a variety of environments without departing from the scope and spirit of the present invention. For example, in one embodiment, the cannulated screw is utilized to secure two fragments of a broken bone together. In another embodiment, the cannulated screw is utilized to secure tissue or a secondary material, such as medical hardware, to a bone. In another embodiment, the cannulated screw is utilized to secure two posts or other members in industrial or construction settings. In yet another embodiment, the cannulated screw is utilized to secure an exterior brace to a patient.

Figure 3:
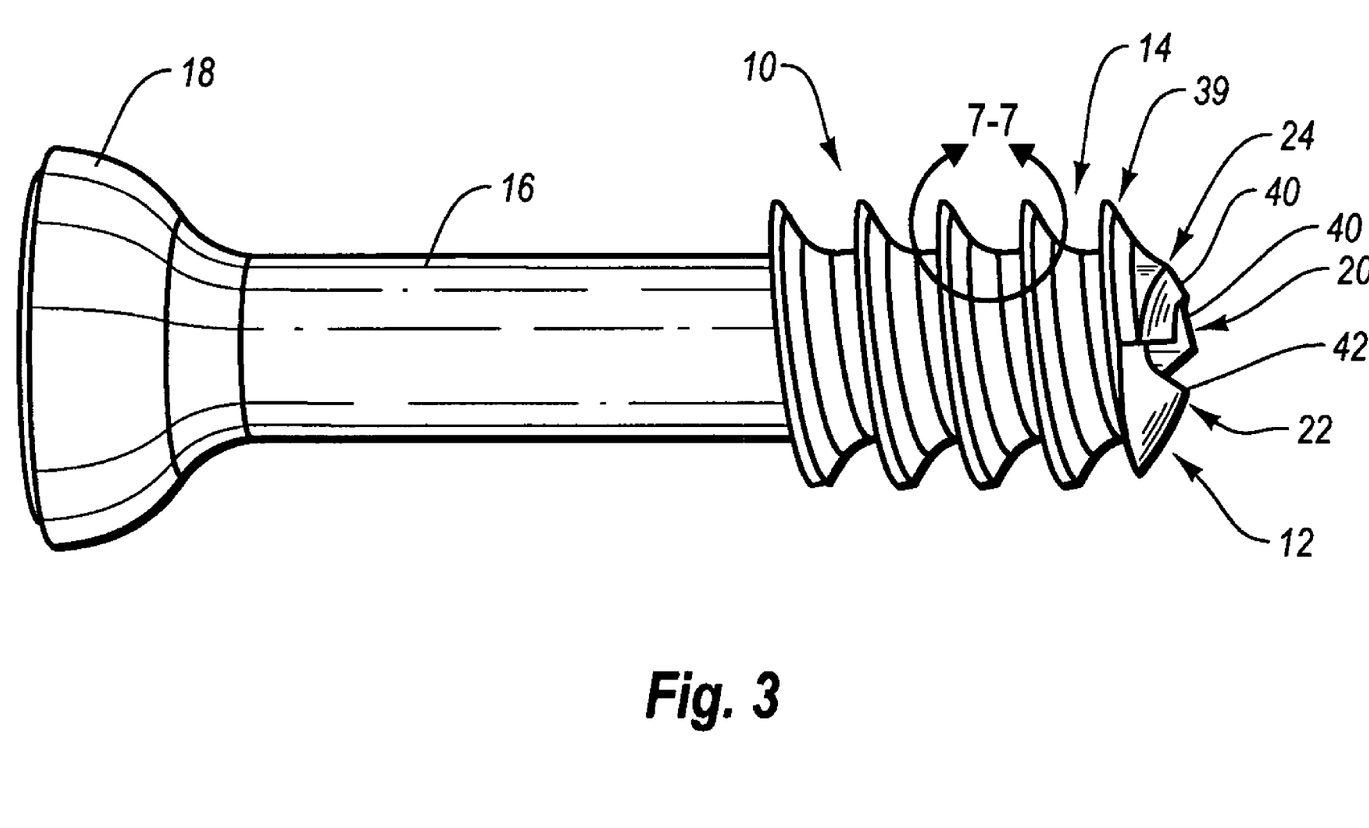
FIG. 3 is a side view of the cannulated screw illustrating the flattened tip portion of the cannulated screw.

FIG. 3 is a side view of a cannulated screw illustrating flattened tip 12, according to one embodiment of the present invention. In the illustrated embodiment, flattened tip 12 comprises a first cutting tooth 20, a second cutting tooth 22, and a third cutting tooth 24. In the illustrated embodiment, first cutting tooth 20, second cutting tooth 22, and cutting tooth 24 comprise progressive cutting teeth which allow for optimized and gradual removal of material, while also facilitating the beginning of threading of the cannulated screw into the material in which cannulated screw 10 is being inserted. First cutting teeth 20, 22, and 24 are an example of a plurality of means for progressive cutting.

Figure 4:
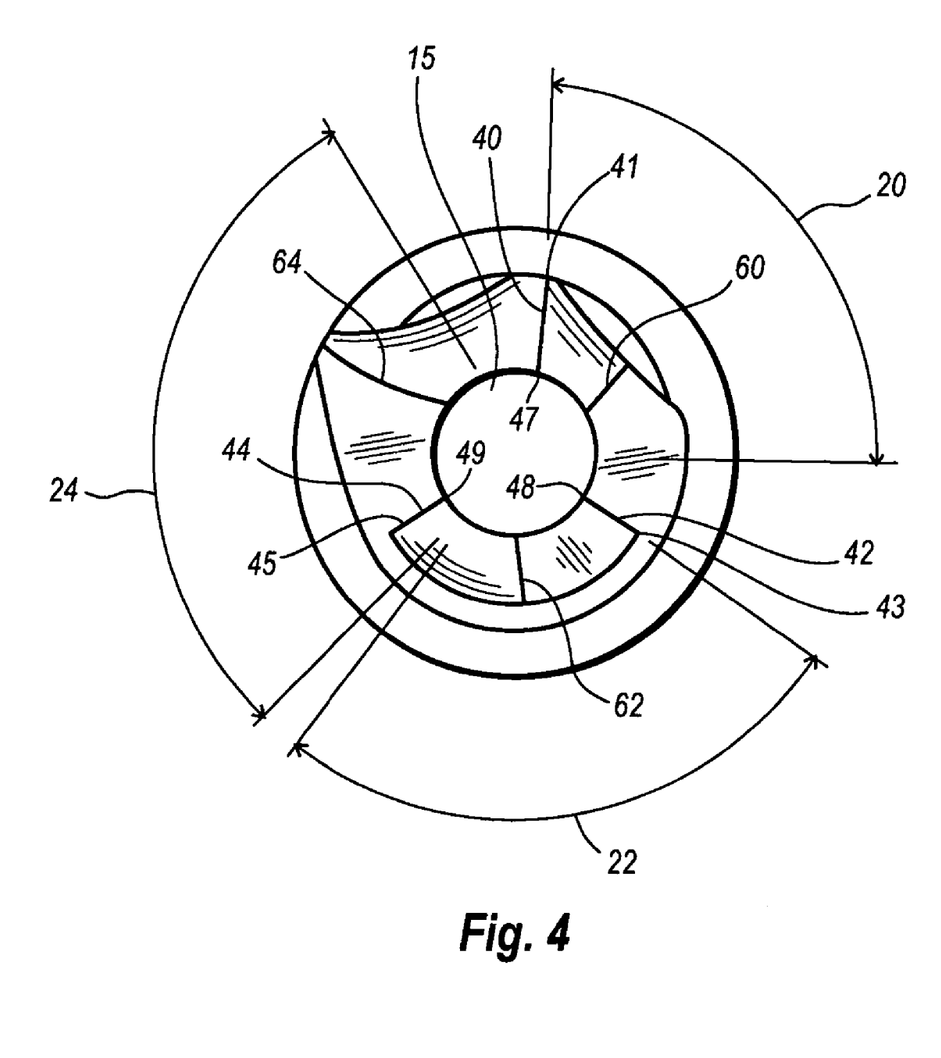
FIG. 4 is a front view of the cannulated screw, illustrating the position of the cutting teeth of the tip of the cannulated screw.

FIG. 4 is a perspective front view of a cannulated screw, according to one embodiment of the present invention. Flattened tip 12 comprises a first cutting tooth 20 having a leading cutting edge 40, a second cutting tooth 22 having a leading cutting edge 42, and a third cutting tooth 24 having a leading cutting edge 44. In the illustrated embodiment, first cutting tooth 20 has the smallest cutting diameter. In other words, one or more dimensions of first cutting tooth 20 are smaller than that of cutting teeth 22 and 24. For example, leading cutting edge 40 of first cutting tooth 20 has the shortest length extending from the inside edge 47 of leading cutting edge 40 to the outside edge 41 of leading cutting edge 40.

In the illustrated embodiment, first cutting tooth 20 includes a ramp edge 60. Ramp edge 60 comprises the angular edge between leading cutting edge 40 and second cutting tooth 22. Ramp edge 60 also forms a portion of the cutting surface of first cutting tooth 20. The angular configuration of ramp edge 60 allows for desired and incremental removal of material as flattened tip 12 is rotated into the material into which cannulated screw 10 is being inserted.

Second cutting tooth 22 and leading cutting edge 42 have an intermediate cutting diameter. In other words, one or more dimensions of second cutting tooth 22 are slightly greater than that of first cutting tooth 20 and slightly smaller than that of third cutting tooth 24. For example, the length of leading cutting edge 42 from the inside edge 48 of leading cutting edge 42 to the outside edge 43 of leading cutting edge 42 is intermediate in length relative to leading cutting edge 40 and leading cutting edge 44.

In the illustrated embodiment, second cutting tooth 22 includes a ramp edge 62. Ramp edge 62 comprises the angular edge between leading cutting edge 42 and third cutting tooth 24. Ramp edge 62 also forms a portion of the cutting surface of second cutting tooth 22. The angular configuration of ramp edge 62 allows for desired and incremental removal of material as flattened tip 12 is rotated into the material into which cannulated screw 10 is being inserted.

Third cutting tooth 24 has the greatest cutting diameter. In other words, one or more dimensions of third cutting tooth 24 is greater than first cutting tooth 20 and second cutting tooth 22. For example, leading cutting edge 44 has a greater length from the inside edge 49 of leading cutting edge 44 to the outside edge 45 of leading cutting edge 44. Leading cutting edges 40, 42, and 44 are examples of a plurality of means for progressive cutting.

In the illustrated embodiment, third cutting tooth 24 includes a ramp edge 64. Ramp edge 64 comprises the angular edge between leading cutting edge 44 and first cutting tooth 20. Ramp edge 64 also forms a portion of the cutting surface of third cutting tooth 24. The angular configuration of ramp edge 64 allows for desired and incremental removal of material as flattened tip 12 is rotated into the material into which cannulated screw 10 is being inserted.

The configuration of first cutting tooth 20 and leading cutting edge 40 is such that a small amount of material is removed as flattened tip 12 is rotated against the material into which cannulated screw 10 is to be inserted. As flattened tip 12 continues to be rotated against the material into which cannulated screw 10 is being inserted, leading cutting edge 42 passes the area through which leading cutting edge 40 has already removed an amount of material. The greater length of leading cutting edge 42 and diameter of second cutting tooth 22 removes an additional amount of material above and beyond that which removed by first cutting tooth 20 and leading cutting edge 40.

As flattened tip 12 continues to be rotated against the material into which cannulated screw 10 is being inserted, third cutting tooth 24 and leading cutting edge 44 pass the area through which the second cutting tooth 22 removed an amount of material. The greater diameter of third cutting tooth 24 and its corresponding leading cutting edge 44 removes yet an additional amount of material. Third cutting tooth 24 also finalizes the beginning of the channel in the material into which the threads of the cannulated screw 10 are inserted.

The configuration of first cutting tooth 20, second cutting tooth 22, and third cutting tooth 24 provide for cutting on contact with the material into which cannulated screw 10 is to be inserted. Additionally, the progressive nature of cutting teeth 20, 22, and 24, provide for desired and optimized removal of material to facilitate insertion of cannulated screw 10 into the material into which the threads of cannulated screw are threaded. In the illustrated embodiment, cutting teeth 20, 22, and 24 correspond with a single thread along the length of the cannulated screw such that the progressive nature of cutting teeth 20, 22, 24 also provides for progressive creation of the channel into which the threads of the cannulated screw are threaded.

Figure 5A:
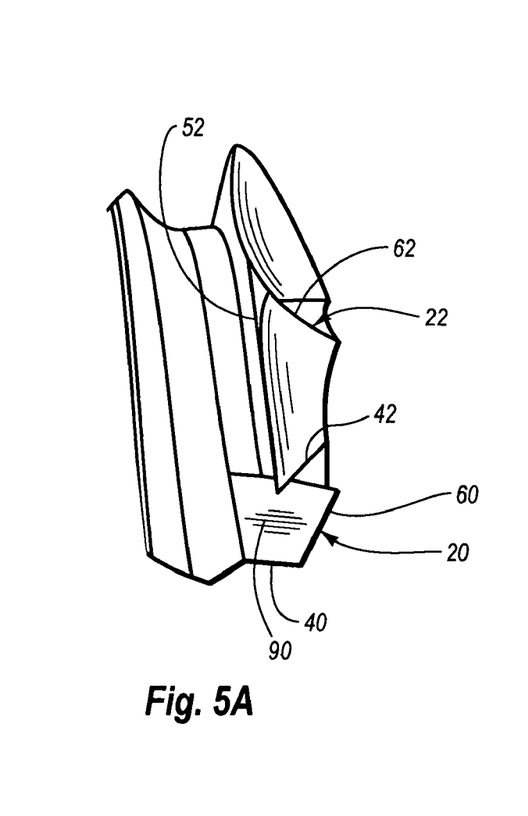
FIG. 5A is close-up side view of the flattened tip of the cannulated screw, illustrating a first cutting tooth and a second cutting tooth.

FIG. 5A is a close-up and side view of flattened tip 12, according to one embodiment of the present invention. In the illustrated embodiment, first cutting tooth 20 and second cutting tooth 22 are illustrated. In the illustrated embodiment, first cutting tooth 20 comprises a leading cutting edge 40, an undercut portion 50, and a ramp edge 60. Leading cutting edge 40 comprises the first surface of first cutting tooth 20 to contact the material to be removed. Leading cutting edge 40 is configured to remove an initial amount of material as first cutting tooth 20 comes in contact with the material into which cannulated screw 10 is being inserted. Undercut portion 50 comprises a recessed portion beneath the main body of first cutting tooth 20. Undercut portion 50 allows for the formation of the beginning of the channel into which the threads of the cannulated screw will be threaded. Ramp edge 60 comprises the angular edge between leading cutting edge 40 and second cutting tooth 22. Ramp edge 60 also forms a portion of the cutting surface of first cutting tooth 20. The angular configuration of ramp edge 60 allows for desired and incremental removal of material as flattened tip 12 is rotated into the material into which cannulated screw 10 is being inserted.

Second cutting tooth 22 is positioned adjacent to first cutting tooth 20. Second cutting tooth 22 comprises a leading cutting edge 42, an undercut portion 52, and a ramp edge 62. Leading cutting edge 42 removes an additional amount of material above and beyond that which is removed by leading cutting edge 40. Undercut portion 52 is configured to provide an additional depth to the channel portion into which threads 14 are inserted. Undercut portion 52 is slightly more pronounced than undercut portion 50 of first cutting tooth 20. Undercut portion 52 provides yet an additional amount of removal of material as desired to provide the threads into which the threads of the cannulated screw are inserted. Ramp edge 60 comprises the angular edge between leading cutting edge 42 and third cutting tooth 24. Ramp edge 62 also comprises a cutting surface that is configured to remove an additional amount of material from that which is removed by ramp edge 60 of first cutting tooth 20. The configuration of ramp edge 62 is adapted to provide a progressive and incremental removal of material in a manner which will minimize breakage or undesired fracturing of bone or other material into which cannulated screw 10 is being inserted.

Figure 5B:
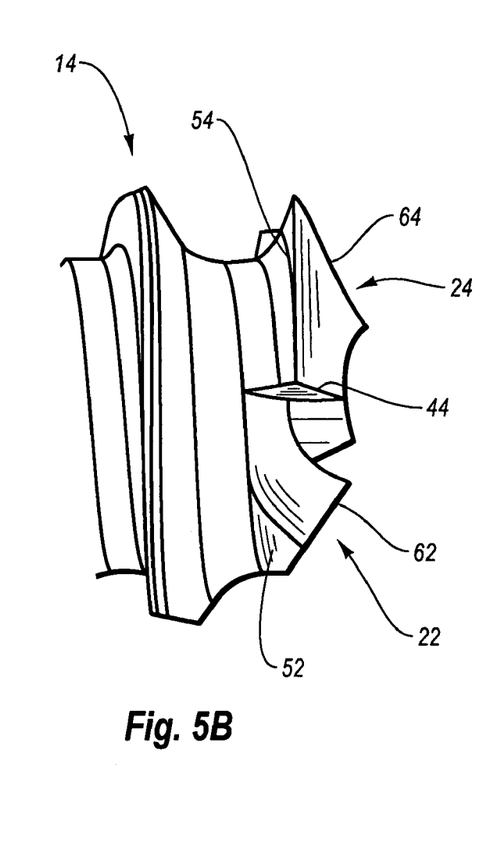
FIG. 5B is a close-up side view of the flattened tip of the cannulated screw illustrating a second cutting tooth and a third cutting tooth.

FIG. 5B illustrates second cutting tooth 22 and third cutting tooth 24, according to one embodiment of the present invention. In the illustrated embodiment, third cutting tooth 24 comprises a leading cutting edge 44, an undercut portion 54, and a ramp edge 64. In the illustrated embodiment, leading cutting edge 44 comprises the leading edge of third cutting tooth 24. Leading cutting edge 44 has a greater height than leading cutting edge 42 to facilitate an additional amount of removal of material above that which provided by leading cutting edge 42. Undercut portion 54 of third cutting tooth 24 provides the channel into which the threads 14 of the cannulated screw 10 are inserted. Ramp edge 64 comprises the angular edge between leading cutting edge 44 and first cutting tooth 20. Ramp portion 64 also provides a cutting surface to remove material above and beyond that which is removed by ramp edge 62. Ramp edge 64 has a more gradual slope to provide an additional degree of cutting by the more angular slope of ramp edge 62.

Figure 5C:
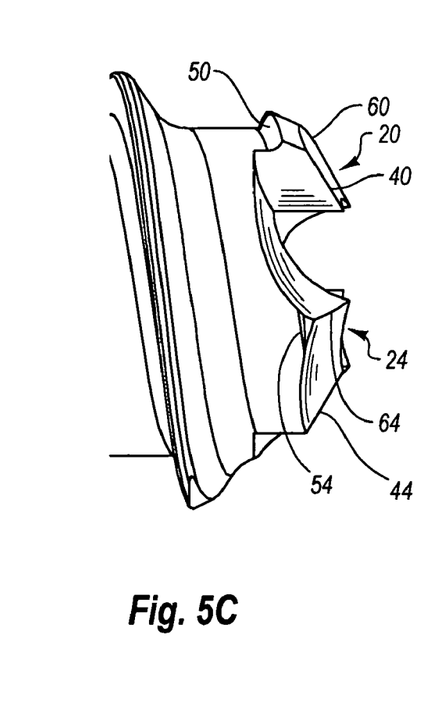
FIG. 5C is a close-up side view of the flattened tip of the cannulated screw illustrating a third cutting tooth and a first cutting tooth.

FIG. 5C is a close-up side view of the flattened tip of the cannulated screw illustrating a third cutting tooth 24 and a first cutting tooth 20. In the illustrated embodiment, third cutting tooth 24 comprises a leading cutting edge 44, an undercut portion 54, and a ramp edge 64. Leading cutting edge 44 comprises the leading edge of third cutting tooth 24. In the illustrated position, third cutting tooth 24 has removed an additional amount of material from that removed by second cutting tooth 22 (see FIG. 5B). Additionally, undercut portion 54 of third cutting tooth 24 has cut the channel into which the threads 14 of the cannulated screw 10 are inserted. In other words, third cutting tooth 24 has finalized the cutting of the material allowing the cannulated screw 10 to advance into the material into which the cannulated screw 10 is being inserted.

In the illustrated embodiment, first cutting tooth 20 is positioned so as to follow third cutting tooth 24 subsequent to rotation of cannulated screw 10. Threads 14 of cannulated screw 10 have raised the position of first cutting tooth 20 above the elevation of third cutting tooth 24. As a result, additional rotation of cannulated screw 10 will remove an additional amount of material than that which was removed by third cutting tooth 24. In other words, the threads 14 of cannulated screw 10 promote additional forward movement and cutting of the teeth 20, 22, and 24 of flattened tip 12.

As will be appreciated by those skilled in the art, a variety of types and configurations of cutting teeth and cutting teeth surfaces can be provided without departing from the scope and spirit of the present invention. For example, in one embodiment of the present invention, the ramp edges of the cutting teeth do not provide an additional cutting surface. In another embodiment, the undercut portions of the cutting teeth do not provide the channel into which the threads are cooperably inserted, but instead provide the threads of the material which are inserted into the channels alternating with the threads of the cannulated screw. According to another embodiment of the present invention, the cutting teeth have essentially the same size, but are positioned at different heights or angles in connections with the threading of the screw to allow for removal of material and advancement of the screw.

Figure 6A:
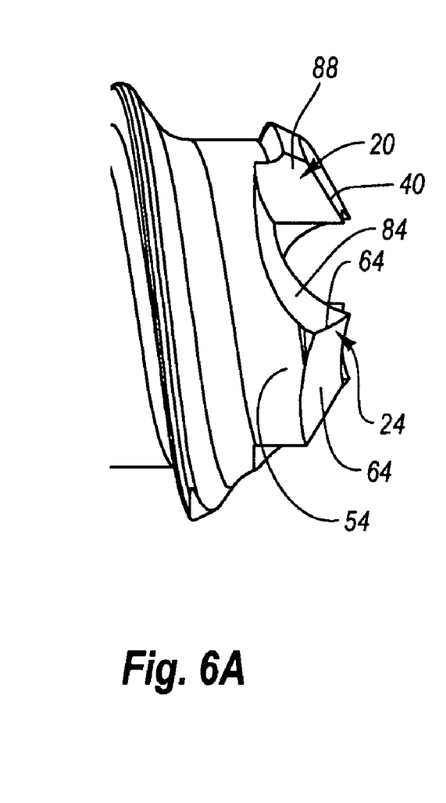
FIG. 6A-6C are close-up side views of the flattened tip of the cannulated screw in different rotational positions illustrating a cutting tooth of the flattened tip from different rotational angles.
Figure 6B:
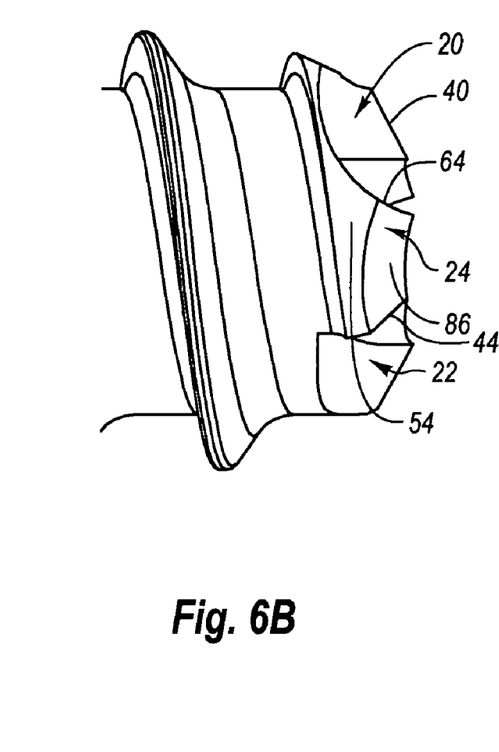
Figure 6C:
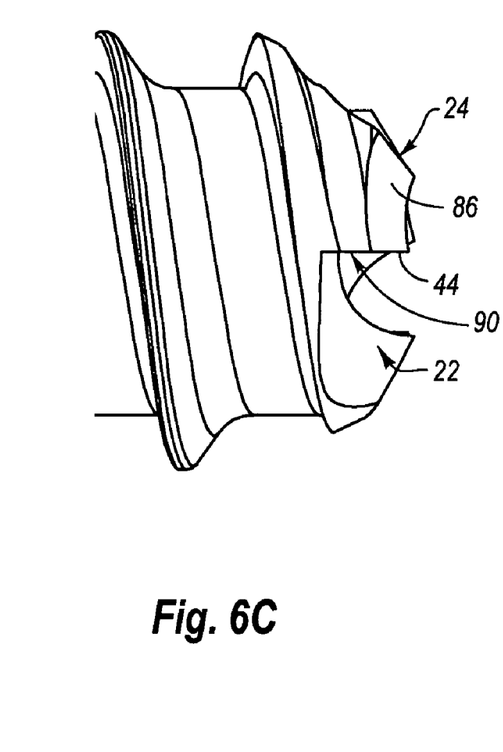

FIG. 6A-6C are close-up side views of the flattened tip 12 of the cannulated screw 10 in different rotational positions illustrating the surfaces of a cutting tooth according to one embodiment of the present invention. FIG. 6A illustrates first cutting tooth 20 and third cutting tooth 24. Third cutting tooth 24 is positioned toward the bottom of the drawing such that ramp edge 64 is clearly depicted. Additionally, a rear sloped surface 84 and a front sloped surface 86 of third cutting tooth 24 are depicted. Front sloped surface 86 slopes from ramp edge 64 in the direction of rotation of cannulated screw 10. Rear sloped surface 84 slopes in the direction away from rotation of the cannulated screw 10. Rear sloped surface 84 and front sloped surface 86 facilitate proper contact between third cutting tooth 24 and the material into which the cannulated screw 10 is being inserted.

In the illustrated embodiment, leading cutting edge 40 and a front surface 88 of the first cutting tooth 20 are shown. Leading cutting edge 40 is the front edge of first cutting tooth 20 which contacts the material which is being removed by first cutting tooth 20. Front surface 88 extends substantially vertically, or at slight angle, downward from leading cutting edge 40. In one embodiment, front surface 88 extends rearward and downward to provide a more distinct and sharp leading cutting edge 40.

FIG. 6B depicts the third cutting tooth 24 in which the rotational position of cannulated screw 10 has been rotated slightly such that third cutting tooth 24 is positioned slightly above the midpoint or center of cannulated screw 10. In the illustrated embodiment, the rotational position of third cutting tooth 24 is such that front sloped surface 86 can be clearly seen while rear sloped surface 84 (see FIG. 6A) is obscured behind ramp edge 64. Front sloped surface 86 slopes from ramp edge 64 to leading cutting edge 44. As third cutting tooth 24 is rotated, leading cutting edge 44 of third cutting tooth 24 contacts the material into which cannulated screw 10 is being inserted and cuts on contact with the material.

FIG. 6C depicts the third cutting tooth 24 in which the rotational position of cannulated screw 10 has been rotated an additional amount such that the third cutting tooth 24 is positioned at the top of the cannulated screw 10. In the illustrated embodiment, the leading edge 44 is shown such that the angle of a front surface 90 can be seen. Front surface 90 extends downward and slightly in a rearward direction from leading edge 44. It can be seen that the length of front surface 90 is greater than the length of front surface 88 of first cutting tooth 20 (see FIG. 6A). The greater length of front surface 90 is due to the progressive nature of cutting teeth 20, 22, and 24. The greater length of front surface 90 allows a greater amount of material to be removed subsequent to cutting with third cutting tooth 24 than that which is removed with first cutting tooth.

As will be appreciated by those skilled in the art, a variety of types and configurations of different flattened tips and cutting teeth can be provided without departing from the scope and spirit of the present invention. For example, in one embodiment, each of the cutting teeth have a single cutting edge. In another embodiment, one or more of the cutting teeth have multiple cutting edges. In another embodiment, the cutting teeth are progressive in nature such that one or more dimensions of the cutting teeth increase from a first cutting tooth to one or more subsequent cutting teeth. In another embodiment, the cutting teeth are progressive in nature but one or more dimensions of the progressive cutting teeth are the same for two or more of the progressive cutting teeth.

Figure 7:
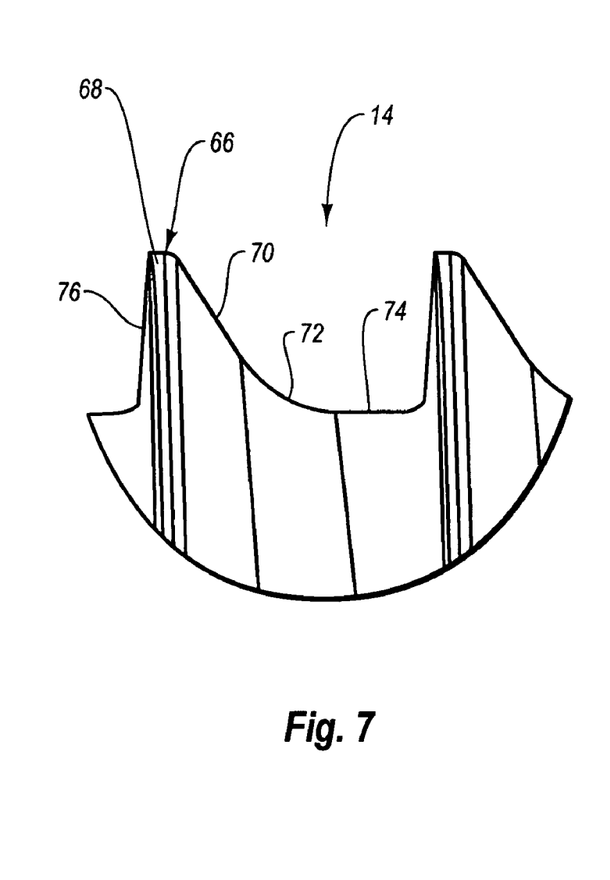
FIG. 7 is a close-up detailed view of the threads of the cannulated screw.

FIG. 7 is a cut-away view taken along line 7-7 of FIG. 3 to illustrate the configuration of threads 14 in greater detail. In the illustrated embodiment, each of threads 14 comprise a thread 66, an outer rim 68, an upper ramp edge 70, a transition surface 77, a trough 74, and a bottom thread surface 76. In the illustrated embodiment, thread 66 represents a single thread which spirals along the entire threaded portion 14 of the cannulated screw. The outer rim 68 of thread 66 comprises the outermost portion which contacts the deepest portion of the channel in the material into which thread 66 is inserted.

Directly adjacent outer rim 68 is provided an upper ramp edge 70. Upper ramp edge 70 has an angular configuration which provides desired cooperative engagement with the channel of the material into which the thread 14 is inserted. Upper ramp edge 70 has a somewhat steep configuration to provide for the sharpened profile of outer rim 68. Adjacent upper ramp edge 70 is positioned transition surface 72. Transition surface 72 has a more gradual slope which provides greater strength and a more frictionless design to thread 66. Transition surface 72 is positioned between upper ramp edge 70 and trough 74. Trough 74 has a substantially horizontal configuration and is adapted to engage the walls of the material into which threads 14 are inserted.

Opposite upper ramp edge 70 is positioned bottom thread surface 76. Bottom thread surface 76 has a substantially perpendicular configuration relative to outer rim 68. The substantially perpendicular configuration of bottom thread surface allows upper ramp edge 70 to continue biasing of thread 66 into the material to allow for continuous self-tapping or boring of the cannulated screw into the material in which it is being inserted.

As will be appreciated by those skilled in the art, a variety of types and configurations of threading of the cannulated screws can be utilized without departing from the scope and spirit of the present invention. For example, the horizontal distance which is covered by the upper ramp edge can exceed that of the combination of the transition surface and trough, according to one embodiment of the present invention. In another embodiment, the lower ramp edge also has a tapered configuration similar to that of the upper ramp edge. In another embodiment, the degree angle of the ramp edges and/or of the pitch of the threads can vary without departing from the scope and spirit of the present invention. In yet another embodiment, a plurality of separated thread lines are provided which correspond with one or more of the plurality of cutting teeth.

Figure 8:
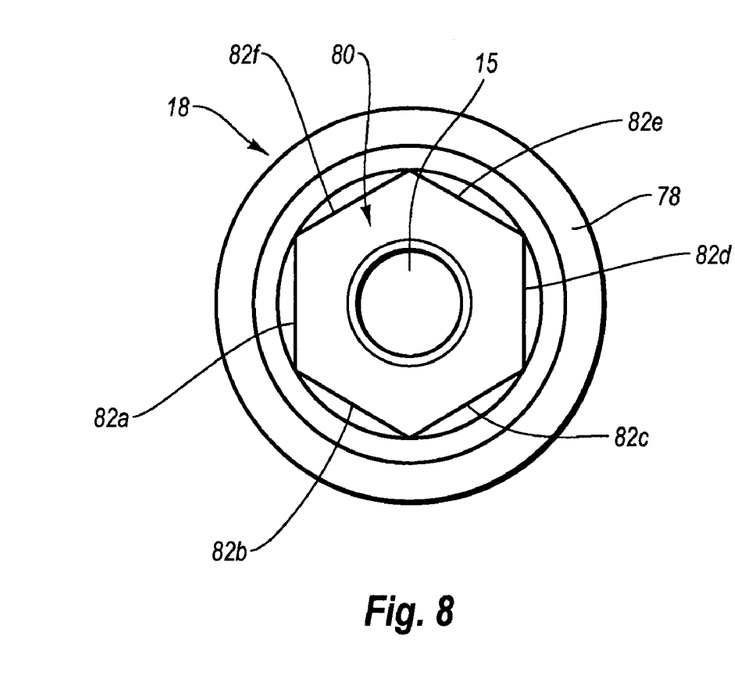
FIG. 8 is a close-up end view of the head of the cannulated screw.

FIG. 8 is close-up end view of head 18 of the cannulated screw, according to one embodiment of the present invention. In the illustrated embodiment, head 18 comprises an outer rim 78 and a rotation tool engagement portion 80. In the illustrated embodiment, outer rim 78 comprises the material from which head 18 is comprised. Rotation tool engagement portion 80 comprises a void into which a rotation tool can be inserted. The rotational tool provides the force vector necessary to rotate the cannulated screw 10 into the material in which the screw is to be inserted.

In the illustrated embodiment, rotation tool engagement portion 80 comprises a plurality of lateral hexagon surfaces 82a-d. Lateral hexagon surfaces 82a-d provide the outer boundary of the rotation tool engagement portion and are configured to be positioned at angles relative to one another. When the rotation tool is inserted into the rotation tool engagement portion 80 and rotated, the rotational tool engages lateral hexagon surfaces 82a-d in a manner so as to provide sufficient rotational torque to rotate the cannulated screw 10. According to one embodiment, the rotational tool is threaded over a guidewire which is positioned in the cannula 15.

As will be appreciated by those skilled in the art, a variety of types and configurations of cannulated screw heads can be utilized without departing from the scope and spirit of the present invention. For example, in one embodiment, a flattened slot is provided in the head of the cannulated screw. In another embodiment, a crossing pattern can be utilized.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A self boring medical fastener for use in a medical setting for securing a first bone to a second bone, the self boring medical fastener adapted to cut on contact with the bone into which the self boring medical fastener is to be inserted to minimize separation at the bone securement interface as the self boring medical fastener passes from one bone to the second bone, the self boring medical fastener comprising:

a cannula having a first portion, a second portion, an inner surface and an outer surface, wherein the first portion of the cannula includes one or more threads positioned in a spiral pattern along a portion of the length thereof, the one or more threads being sized and configured to secure the cannula to a bone, and wherein the second portion of the cannula is devoid of threads;

an end of the cannula adjacent the second portion of the cannula comprising a head, the head extending radially outward from the cannula and being adapted to accommodate a rotational tool which provides the rotational force necessary to allow for self boring of the self boring medical fastener into material in which the self boring medical fastener is to be positioned; and an end of the cannula opposite the head and adjacent the one or more threads comprising a tip, the tip having at least three cutting teeth, each of the cutting teeth comprising: (i) a continuous leading cutting edge extending from the inner surface of the cannula at the tip, (ii) a ramp edge extending from the inner surface of the cannula at the tip, and (iii) a curved cutting surface extending from the leading cutting edge up to the ramp edge, wherein the continuous leading cutting edge and the curved cutting surface of each tooth are configured to cut material to form a path in a bone into which the one or more threads will follow as the self boring medical fastener is advanced into the bone;

wherein a slope of the curved cutting surface from the leading cutting edge to the ramp edge of each cutting tooth gradually increases from a first tooth of the at least three cutting teeth to subsequent teeth of the at least three cutting teeth.

2. The self-boring medical fastener of claim 1, wherein the at least three cutting teeth adapted to cut on contact with the material into which the medical fastener is to be positioned.

3. The self-boring medical fastener of claim 1, wherein the at least three cutting teeth minimize the amount of normal force against the material needed to allow for self-boring of the medical fastener that could result in displacement of the material as a result of contact with the self-boring medical fastener.

4. The self-boring medical fastener of claim 1, wherein the at least three cutting teeth comprise three progressive cutting teeth.

5. The self-boring medical fastener of claim 4, wherein the three progressive cutting teeth comprise a first cutting tooth having a first dimension to remove a first amount of material and second and third progressive cutting teeth having a greater dimension to remove an additional amount of material to provide self-boring of the medical fastener.

6. The self-boring medical fastener of claim 4, wherein the three progressive cutting teeth consist of a first cutting tooth, a second cutting tooth, and a third cutting tooth.

7. The self-boring medical fastener of claim 5, wherein the first cutting tooth has the smallest cutting dimension, the second cutting tooth has an intermediate cutting dimension, and the third cutting tooth has the greatest cutting dimension.

8. The self-boring medical fastener of claim 1, further comprising a recess extending from the head of the self-boring medical fastener axially toward the tip, the recess being configured to receive a portion of the rotational tool.

9. The self-boring medical fastener of claim 1, wherein the tip is flattened such the distance between the uppermost surface of the tip and the uppermost surface of the threads is less than the one and half times the distance between adjacent threads on the cannula.

10. The self-boring medical fastener of claim 1, wherein a length that each leading cutting edge of each tooth extends from the inner surface of the cannula increases from a first tooth of the at least three cutting teeth to subsequent teeth of the at least three cutting teeth.

11. A self boring medical fastener for use in a medical setting and being adapted to cut on contact with the material into which the self boring medical fastener is to be inserted, the self boring medical fastener comprising, a cannula having an inner surface, an outer surface, and one or more threads positioned in a spiral pattern along a portion of the length of the cannula, the one or more threads being sized and configured to secure the cannula to a bone, and wherein another portion of the length of the cannula is devoid of threads;

an end of the cannula comprising a head, the head being adapted to accommodate a rotational tool which provides the rotational force necessary to drive the self boring medical fastener into material in which the self boring medical fastener is to be positioned; and an end of the cannula opposite the head comprising a tip, the tip having a length that is less than one and half times the distance between adjacent threads along the length of the cannula, the tip comprising at least three progressive cutting teeth which cut on contact with the material into which the medical fastener is to be positioned, wherein a first cutting tooth has a continuous first leading cutting edge, a first ramp edge, and a curved cutting surface extending from the first leading edge to the ramp edge, wherein the first leading cutting edge extends from the inner surface of the cannula at the tip a first radial distance, and the first ramp edge extends from the inner surface of the cannula at the tip a second radial distance greater than the first radial distance, and each additional tooth of the at least three progressive cutting teeth provide a leading cutting edge extending from the inner surface of the cannula at the tip a radial distance greater than the first radial distance to remove an additional amount of material to provide self-boring of the medical fastener such that the cutting of the at least three cutting teeth minimizes the normal force against the material allowing for self-boring of the medical fastener while minimizing pressure against the material that could otherwise result in displacement of the material as a result of the contact with the self-boring medical fastener.

12. The self-boring medical fastener of claim 11, wherein the self-boring tip has a flattened configuration to reduce the distance between the uppermost surface of the tip and the average plane of a first thread of the cannula such that additional threads can engage a cortical layer of a bone before the self-boring tip exits the outward surface of the cortical layer.

13. The self-boring medical fastener of claim 11, wherein the at least three progressive cutting teeth consist of the first cutting tooth, a second cutting tooth, and a third cutting tooth.

14. The self-boring medical fastener of claim 13, wherein each of the first cutting tooth, the second cutting tooth, and the third cutting tooth has an upper cutting edge, a tapered cutting portion, and an undercut portion.

15. A self boring medical fastener for use in a medical setting and being adapted to cut on contact with the material into which the self boring medical fastener is to be inserted, the self boring medical fastener comprising,
a cannula having an inner surface, outer surface, a neck portion devoid of threads, and one or more threads positioned in a spiral pattern along another portion of the length of the cannula, the one or more threads being sized and configured to secure the cannula to a bone;
an end of the cannula comprising a head, the head extending radially outward from the outer surface of the cannula, the head being adapted to accommodate a rotational tool which provides the rotational force necessary to drive the self boring medical fastener into material in which the self boring medical fastener is to be positioned; and
an end of the cannula opposite the head comprising a self-boring tip, the self-boring tip having a at least three teeth for progressive cutting, wherein a first cutting tooth has a continuous first leading cutting edge and a first ramp edge, and a first curved cutting surface extending from the first leading edge to the ramp edge, wherein the first leading cutting edge extends from the inner surface of the cannula radially and axially a first distance, and wherein each additional tooth of the at least three teeth for progressive cutting provides a leading cutting edge that extends from the inner surface of the cannula radially and axially a distance greater than the first distance, wherein the at least three teeth for progressive cutting provide self-boring of the medical fastener while minimizing pressure against the material that could otherwise result in displacement of the material as a result of the contact with the self-boring medical fastener.

16. The self boring medical fastener of claim 15, wherein the at least three teeth for progressive cutting comprise cutting teeth with a cutting surface between a leading edge and a ramp edge positioned at a slope which gradually increases between teeth.

17. The self boring medical fastener of claim 15, wherein the at least three teeth for progressive cutting comprise cutting surfaces.

18. The self boring medical fastener of claim 15, wherein the self boring medical fastener comprises a screw.

* * * * *

UNITED STATES PATENT AND TRADEMARK OFFICE
CERTIFICATE OF CORRECTION

| | | |
|---|---|---|
| PATENT NO. | : 7,731,738 B2 | Page 1 of 2 |
| APPLICATION NO. | : 11/298065 | |
| DATED | : June 8, 2010 | |
| INVENTOR(S) | : Jackson et al. | |

It is certified that error appears in the above-identified patent and that said Letters Patent is hereby corrected as shown below:

Drawings
Sheet 3, replace Figure 3 with the figure depicted below, wherein one of the two numbers "40" and the number "39" have been deleted

Fig. 3

Signed and Sealed this
Twenty-sixth Day of May, 2015

Michelle K. Lee
*Director of the United States Patent and Trademark Office*

CERTIFICATE OF CORRECTION (continued)

U.S. Pat. No. 7,731,738 B2

Sheet 6, replace Figure 6A with the figure depicted below, wherein bottom number "64" has been changed to --86--

Fig. 6A

In the Specification

Column 12
Line 22, change "77" to --72--